US010315969B2

(12) United States Patent
Hwang et al.

(10) Patent No.: US 10,315,969 B2
(45) Date of Patent: Jun. 11, 2019

(54) METHOD OF PREPARING MULTICOMPONENT COMPOSITE METAL OXIDE CATALYST

(71) Applicant: LG CHEM, LTD., Seoul (KR)

(72) Inventors: Ye Seul Hwang, Daejeon (KR); Dong Hyun Ko, Daejeon (KR); Kyong Yong Cha, Daejeon (KR); Dae Heung Choi, Daejeon (KR); Myung Ji Suh, Daejeon (KR); Jun Han Kang, Daejeon (KR); Joo Hyuck Lee, Daejeon (KR); Hyun Seok Nam, Daejeon (KR); Jun Kyu Han, Daejeon (KR); Sang Jin Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 444 days.

(21) Appl. No.: 14/900,290

(22) PCT Filed: Jun. 4, 2015

(86) PCT No.: PCT/KR2015/005625
§ 371 (c)(1),
(2) Date: Dec. 21, 2015

(87) PCT Pub. No.: WO2015/190754
PCT Pub. Date: Dec. 17, 2015

(65) Prior Publication Data
US 2016/0368839 A1    Dec. 22, 2016

(30) Foreign Application Priority Data

Jun. 10, 2014 (KR) .......................... 10-2014-0070222
Jun. 4, 2015 (KR) .......................... 10-2015-0079139

(51) Int. Cl.
*C07C 5/333* (2006.01)
*B01J 23/887* (2006.01)
(Continued)

(52) U.S. Cl.
CPC ........... *C07C 5/3332* (2013.01); *B01J 23/002* (2013.01); *B01J 23/881* (2013.01);
(Continued)

(58) Field of Classification Search
CPC .......... C07C 5/3332; C07C 5/48; B01J 37/03; B01J 37/031; B01J 37/04; B01J 37/08;
(Continued)

(56) References Cited

U.S. PATENT DOCUMENTS 3,764,632 A    10/1973  Takenaka et al.
3,932,551 A    1/1976   Grasselli et al.
(Continued)

FOREIGN PATENT DOCUMENTS

CN    103274888 A    9/2013
CN    103298771 A    9/2013
(Continued)

*Primary Examiner* — Jun Li
(74) *Attorney, Agent, or Firm* — Dentons US LLP

(57) ABSTRACT

Provided are a method of preparing a multicomponent bismuth-molybdenum composite metal oxide catalyst, and a multicomponent bismuth-molybdenum composite metal oxide catalyst prepared thereby. According to the preparation method, since the almost same structure as that of a typical quaternary bismuth-molybdenum catalyst may be obtained by performing two-step co-precipitation, i.e., primary and secondary co-precipitation, of metal components constituting the catalyst, the reduction of catalytic activity due to the deformation of the structure of the catalyst may be suppressed. Also, since the multicomponent bismuth-molybdenum composite metal oxide catalyst may adjust the number of lattice oxygens consumed during a reaction to increase the catalytic activity, the multicomponent bismuth-molybdenum composite metal oxide catalyst may reduce the formation of by-products and may improve the conversion rate of reactant and the yield of desired product in a catalytic reaction process using the above catalyst, particularly, a (Continued)

catalytic reaction process under a relatively low temperature condition.

9 Claims, 7 Drawing Sheets

(51) Int. Cl.
    *B01J 37/03*     (2006.01)
    *B01J 37/04*     (2006.01)
    *B01J 37/08*     (2006.01)
    *B01J 23/00*     (2006.01)
    *B01J 23/881*     (2006.01)
    *B01J 35/00*     (2006.01)
    *C07C 5/48*     (2006.01)

(52) U.S. Cl.
    CPC ......... *B01J 23/8876* (2013.01); *B01J 35/002* (2013.01); *B01J 35/0006* (2013.01); *B01J 37/03* (2013.01); *B01J 37/031* (2013.01); *B01J 37/04* (2013.01); *B01J 37/08* (2013.01); *B01J 37/088* (2013.01); *C07C 5/48* (2013.01); *B01J 37/035* (2013.01); *B01J 2523/00* (2013.01); *C07C 2523/31* (2013.01); *C07C 2523/887* (2013.01)

(58) Field of Classification Search
    CPC .... B01J 23/8876; B01J 23/002; B01J 23/881; B01J 2523/00
    See application file for complete search history.

(56) References Cited

U.S. PATENT DOCUMENTS

| | | | | |
|---|---|---|---|---|
| 4,280,928 A | * | 7/1981 | Kirch | B01J 23/8876 502/205 |
| 4,657,885 A | * | 4/1987 | Fiato | B01J 23/80 502/241 |
| 5,245,083 A | | 9/1993 | Matsuura | |
| 6,583,316 B1 | * | 6/2003 | Onodera | B01J 23/002 562/537 |
| 9,205,414 B2 | * | 12/2015 | Kawano | B01J 23/002 |
| 2007/0161842 A1 | * | 7/2007 | Johann | C07C 5/327 585/658 |
| 2007/0167321 A1 | * | 7/2007 | Tatsumi | B01J 23/002 502/321 |
| 2007/0167661 A1 | * | 7/2007 | Johann | C07C 5/333 585/616 |
| 2010/0099936 A1 | * | 4/2010 | Shin | B01J 23/002 585/631 |
| 2010/0125161 A1 | | 5/2010 | Chung et al. | |
| 2012/0078026 A1 | | 3/2012 | Midorikawa et al. | |
| 2013/0281748 A1 | | 10/2013 | Cha et al. | |
| 2014/0114108 A1 | * | 4/2014 | Yano | C07C 5/48 585/506 |

FOREIGN PATENT DOCUMENTS

| | | |
|---|---|---|
| CN | 103483131 | 1/2014 |
| CN | 103483133 | 1/2014 |
| EP | 2711350 A1 | 3/2014 |
| EP | 2727899 A1 | 5/2014 |
| JP | 2013527141 A | 6/2013 |
| KR | 20080105286 A | 12/2008 |
| KR | 10-2010-0028702 A | 3/2010 |
| KR | 10-1086731 B1 | 11/2011 |
| KR | 20120073733 A | 7/2012 |
| KR | 10-2013-0003125 A | 1/2013 |
| WO | 20130161702 | 10/2013 |

* cited by examiner

METHOD OF PREPARING MULTICOMPONENT COMPOSITE METAL OXIDE CATALYST

CROSS-REFERENCE TO RELATED APPLICATIONS

This application is a National Stage Entry of International Application No. PCT/KR2015/005625, filed Jun. 4, 2015, and claims the benefit of and priority to Korean Patent Application No. 10-2014-0070222, filed Jun. 10, 2014, and Korean Patent Application No. 10-2015-0079139, filed Jun. 4, 2015, all of which are incorporated herein by reference in their entirety for all purposes as if fully set forth herein.

TECHNICAL FIELD

The present invention relates to a method of preparing a multicomponent bismuth-molybdenum composite metal oxide catalyst which includes the steps of preparing a second solution by dropwise adding a first solution, in which a divalent or trivalent cationic metal precursor solution, a monovalent cationic metal precursor solution, and a bismuth precursor solution are mixed, to a molybdenum precursor solution and performing primary co-precipitation; and dropwise adding a third solution including a tetravalent cationic metal having oxygen storability and oxygen mobility to the second solution and performing secondary co-precipitation, and a multicomponent bismuth-molybdenum composite metal oxide catalyst prepared thereby.

BACKGROUND ART

A selective oxidation reaction of olefin occupies an important position in the petrochemical industry as a reaction capable of preparing an intermediate base material required for producing various products from an olefin raw material. A significant amount of research into a process of preparing styrene from ethyl benzene and a process of preparing 1,3-butadiene from n-butane or n-butene in the above reaction has been conducted as the recent demand for a base material for preparing a synthetic rubber has rapidly grown. In particular, since the demand for 1,3-butadiene has rapidly grown, there is a need to develop a technique for securing a sufficient amount of the 1,3-butadiene.

1,3-butadiene, a colorless and odorless flammable gas, is a material that is easily liquefied when the pressure is applied and is easily flammable, wherein it is a very important feedstock used as a raw material of various petrochemical products, for example, synthetic rubbers such as styrene-butadiene rubber (SBR), polybutadiene rubber (BR), and acrylonitrile-butadiene-styrene rubber (ABS).

As a method of preparing 1,3-butadiene, there are broadly naphtha cracking, direct dehydrogenation of n-butene, or oxidative dehydrogenation of n-butene. Among the above methods, the naphtha cracking responsible for 90% or more of 1,3-butadiene supplied to the market is performed in such a manner that 1,3-butadiene is selectively extracted from a feed stock which is produced from a cracker in a steam cracking process for the production of ethylene. However, since the main purpose of the steam cracking process is for the production of feedstocks other than 1,3-butadiene, the production of 1,3-butadiene by the steam cracking process may not be an effective process for producing 1,3-butadiene and a lot of energy consumption may be required due to a high reaction temperature. Accordingly, dehydrogenation has been received attention in which 1,3-butadiene is obtained by removing hydrogen from n-butene in a C4 mixture (C4 raffinate-3) which is remained after extracting all of the useful feedstocks in the steam cracking process. The dehydrogenation of n-butene includes direct dehydrogenation and oxidative dehydrogenation. The direct dehydrogenation of n-butene is a reaction of obtaining 1,3-butadiene by removing hydrogen from the n-butene, wherein the direct dehydrogenation has a limitation in that a high-temperature reaction condition is required due to a limited conversion rate because the direct dehydrogenation is thermodynamically unfavorable as a highly endothermic reaction, and the yield of 1,3-butadiene may be reduced because a side reaction, such as an idealized reaction, is increased due to an increase in the temperature even if the conversion rate is increased by increasing the temperature.

The oxidative dehydrogenation (ODH) of n-butene, which produces butadiene through the ODH of n-butene, is a reaction in which n-butene and oxygen are reacted to generate 1,3-butadiene and water, wherein the oxidative dehydrogenation of n-butene may not only be thermodynamically favorable because stable water is generated after the reaction, but may also obtain 1,3-butadiene with a high yield even at a lower reaction temperature than the direct dehydrogenation because it is an exothermic reaction different from the direct dehydrogenation. Thus, a process of producing 1,3-butadiene through the oxidative dehydrogenation of n-butene may be considered as an effective single production process which may meet the increasing demand of 1,3-butadiene.

As described above, since the oxidative dehydrogenation uses oxygen as a reactant even though it is an effective process capable of preparing 1,3-butadiene alone, the oxidative dehydrogenation may have a limitation in that a lot of side reactions, such as complete oxidation, occur. Thus, there is a need to develop a catalyst having high selectivity to 1,3-butadiene while maintaining high activity through the appropriate control of oxidation ability.

Current known catalysts used in the oxidative dehydrogenation of n-butene include a ferrite-based catalyst, a tin-based catalyst, and a bismuth-molybdenum-based catalyst.

Among the above catalysts, the bismuth-molybdenum-based catalyst includes a bismuth-molybdenum catalyst only composed of bismuth and molybdenum oxides and a multicomponent bismuth-molybdenum catalyst in which various metal components are added on the basis of bismuth and molybdenum. Various phases are present in a pure bismuth-molybdenum catalyst depending on an atomic ratio of bismuth to molybdenum, wherein it is known that three phases of α-bismuth molybdenum ($Bi_2Mo_3O_{12}$), β-bismuth molybdenum ($Bi_2Mo_2O_9$), and γ-bismuth molybdenum ($Bi_2MoO_6$) may be used as the above catalyst. However, a single-phase pure bismuth-molybdenum catalyst is not suitable for a commercialization process of preparing 1,3-butadien through the oxidative dehydrogenation of n-butene due to its low activity.

As an alternative, the preparation of a multicomponent bismuth-molybdenum catalyst, in which various metal components in addition to bismuth and molybdenum are added, has been attempted. Examples of the multicomponent bismuth-molybdenum catalyst may be a composite oxide catalyst composed of nickel, cesium, bismuth, and molybdenum, a composite oxide catalyst composed of cobalt, iron, bismuth, magnesium, potassium, and molybdenum, and a composite oxide catalyst composed of nickel, cobalt, iron, bismuth, phosphorous, potassium, and molybdenum.

The typical multicomponent bismuth-molybdenum catalyst as described above has been prepared by one-step co-precipitation of various metal precursors. However, in a case in which a multicomponent bismuth-molybdenum catalyst having complex components is prepared by one-step co-precipitation, the reproducibility of the preparation of the catalyst may not only be reduced because it may be difficult to uniformly form catalyst components, but economic efficiency may also be reduced because catalytic activity per unit mass may be reduced due to a low specific surface area of the catalyst. Also, in a case in which the reaction is performed in a temperature range of 320° C. to 520° C. or less, as a typical reaction temperature range, in order to increase the economic efficiency by reducing energy consumption, the catalytic activity may be reduced. Thus, in order to increase the economic efficiency, there is a need to develop a technique which may prepare a catalyst in which catalyst components are uniformly formed and its catalytic activity is not reduced under a relatively low temperature condition.

Under the above-described background, while conducting research into a method of preparing a catalyst which may appropriately control oxidation ability without a reduction in catalytic activity even at a relatively low temperature, the present inventors have confirmed that a multicomponent bismuth-molybdenum composite metal oxide catalyst, which is prepared by a method consisting of a two-step co-precipitation process that includes the steps of preparing a second solution by dropwise adding a first solution including a divalent or trivalent cationic metal precursor, a monovalent cationic metal precursor, and a bismuth precursor to a solution including a molybdenum precursor and performing primary co-precipitation; and dropwise adding a third solution including a tetravalent cationic metal precursor represented by Formula 2 and performing secondary co-precipitation, exhibits excellent catalytic activity even under a relatively low temperature condition while having the almost same structure as a typical quaternary bismuth-molybdenum catalyst, thereby leading to the completion of the present invention.

DISCLOSURE OF THE INVENTION

Technical Problem

The present invention provides a method of preparing a multicomponent bismuth-molybdenum composite metal oxide catalyst having excellent catalytic activity even under a relatively low reaction temperature condition which includes the steps of preparing a second solution by dropwise adding a first solution, in which a divalent or trivalent cationic metal precursor solution, a monovalent cationic metal precursor solution, and a bismuth precursor solution are mixed, to a molybdenum precursor solution and performing primary co-precipitation; and dropwise adding a third solution including a tetravalent cationic metal having oxygen storability and oxygen mobility to the second solution and performing secondary co-precipitation.

The present invention also provides a multicomponent bismuth-molybdenum composite metal oxide catalyst prepared by the above-described two-step co-precipitation.

The present invention also provides a method of preparing 1,3-butadiene using the multicomponent bismuth-molybdenum composite metal oxide catalyst.

Technical Solution

According to an aspect of the present invention, there is provided a method of preparing a multicomponent bismuth-molybdenum composite metal oxide catalyst represented by Formula 1 including the steps of: preparing a first solution by mixing a divalent or trivalent cationic metal precursor solution, a monovalent cationic metal precursor solution, and a bismuth precursor solution (step 1); preparing a second solution by dropwise adding the first solution to a molybdenum precursor solution and performing primary co-precipitation (step 2); preparing a fourth solution by dropwise adding a third solution including a tetravalent cationic metal precursor during an aging process of the second solution and performing secondary co-precipitation (step 3); and sintering after drying the fourth solution (step 4).

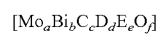
[Formula 1]

in Formula 1,
C represents a divalent or trivalent cationic metal element,
D represents a monovalent cationic metal element,
E represents a tetravalent cationic metal element,
a is a real number of 5 to 20, b is a real number of 0.1 to 2, c is a real number of 1 to 5, d is a real number of 1 to 10, e is a real number of 0.1 to 1, and f is a value which is determined by other components to match valency.

According to another aspect of the present invention, there is provided a multicomponent bismuth-molybdenum composite metal oxide catalyst represented by Formula 1 which is prepared by the above method.

According to another aspect of the present invention, there is provided a method of preparing 1,3-butadiene including the steps of: filling a reactor with the multicomponent bismuth-molybdenum composite metal oxide catalyst as a stationary phase (step A); and performing oxidative dehydrogenation while continuously passing a reactant, which contains a C4 compound including n-butene, through a catalyst layer of the reactor filled with the catalyst (step B).

Advantageous Effects

Since a method of preparing a multicomponent bismuth-molybdenum composite metal oxide catalyst according to the present invention may facilitate the uniform formation of metal components in the catalyst by performing two-step co-precipitation, i.e., primary and secondary co-precipitation, of the metal components constituting the catalyst, the reproducibility of the preparation of the catalyst may be excellent.

Also, since the multicomponent bismuth-molybdenum composite metal oxide catalyst prepared by the above method may have the almost same structure as that of a quaternary bismuth-molybdenum catalyst, the reduction of catalytic activity due to the deformation of the structure of the catalyst may be suppressed. Since the multicomponent bismuth-molybdenum composite metal oxide catalyst may include a component having oxygen storability and oxygen mobility without the deformation of the structure of the catalyst, it may have high hydrothermal stability. Furthermore, since the multicomponent bismuth-molybdenum composite metal oxide catalyst may adjust the number of lattice oxygens of the catalyst consumed during the reaction to increase the catalytic activity, the multicomponent bismuth-molybdenum composite metal oxide catalyst may reduce the formation of by-products and may improve the conversion rate of reactant and the yield of desired product in a catalytic reaction process using the above catalyst, particularly, a catalytic reaction process under a relatively low temperature condition.

Thus, the method of preparing a multicomponent bismuth-molybdenum composite metal oxide catalyst according to the present invention and the catalyst prepared thereby may be suitable for the industry requiring the above method and catalyst, particularly, the 1,3-butadiene production industry.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Figure 1:
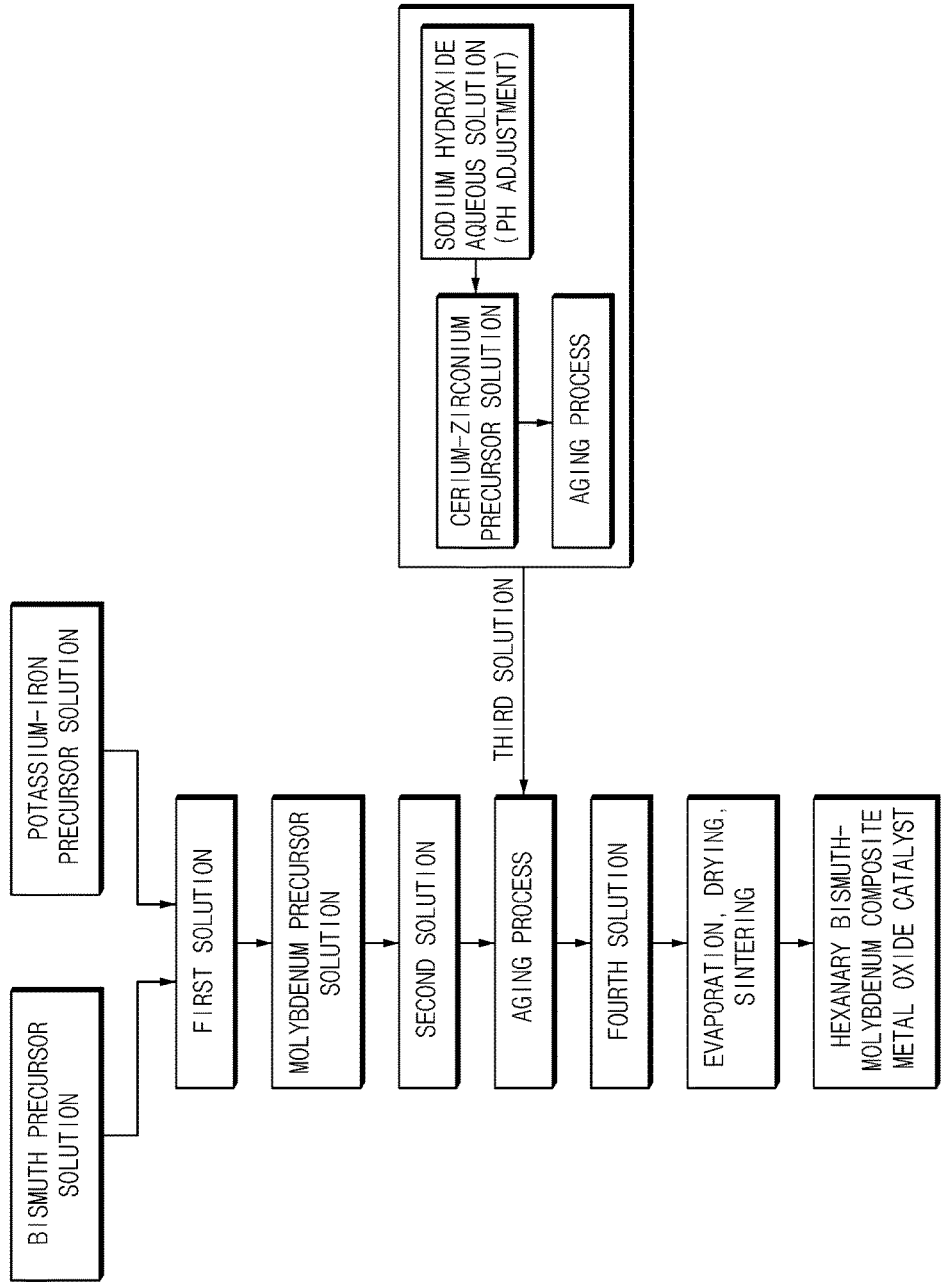
FIG. 1 is a flowchart schematically illustrating a method of preparing a multicomponent bismuth-molybdenum composite metal oxide catalyst according to an embodiment of the present invention.

Hereinafter, the present invention will be described in more detail to allow for a clearer understanding of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention provides a method of preparing a multicomponent bismuth-molybdenum composite metal oxide catalyst having excellent activity even in a catalytic reaction process under a relatively low temperature condition which includes the steps of preparing a second solution by dropwise adding a first solution including a divalent or trivalent cationic metal precursor, a monovalent cationic metal precursor, and a bismuth precursor to a molybdenum precursor solution and performing primary co-precipitation; and dropwise adding a third solution including a tetravalent cationic metal precursor to the second solution and performing secondary co-precipitation.

In general, as a method of preparing 1,3-butadiene, there are broadly naphtha cracking, direct dehydrogenation of n-butene, or oxidative dehydrogenation of n-butene. Among them, since stable water is generated as a product during the oxidative dehydrogenation of n-butene, the oxidative dehydrogenation of n-butene is thermodynamically favorable.

Also, since oxidative dehydrogenation is an exothermic reaction different from direct dehydrogenation, 1,3-butadiene may be obtained with a relatively high yield even at a relatively low temperature of 320° C. to 520° C. in comparison to the direct dehydrogenation. Thus, the oxidative dehydrogenation is on the spotlight as an effective process.

However, as described above, since the oxidative dehydrogenation uses oxygen as a reactant, the oxidative dehydrogenation may have a limitation in that a lot of side reactions, such as complete oxidation, occur. Thus, in order to easily use the oxidative dehydrogenation as a commercialization process, there is a need to develop a catalyst having high selectivity to 1,3-butadiene while maintaining high activity through the appropriate control of oxidation ability, and, simultaneously, in order to use the oxidative dehydrogenation as a more efficient and economical commercialization process, there is a need to develop a catalyst which may maintain high conversion rate and yield even at a lower reaction temperature.

Currently, a ferrite-based catalyst, a tin-based catalyst, and a bismuth-molybdenum-based catalyst are used in the oxidative dehydrogenation, and although a single-phase pure bismuth-molybdenum catalyst is used as the bismuth-molybdenum-based catalyst among the above catalysts, the commercialization of the single-phase pure bismuth-molybdenum catalyst is difficult due to its low catalytic activity. As an alternative, a multicomponent bismuth-molybdenum catalyst has been proposed in which various metal components are added. However, since a typical multicomponent bismuth-molybdenum catalyst is prepared by one-step co-precipitation of various metal precursors, the reproducibility of the preparation of the catalyst may be reduced because it is difficult to uniformly form a plurality of metal components in the catalyst. Also, since the typical multicomponent bismuth-molybdenum catalyst has a structure different from that of a typical single-phase quaternary bismuth-molybdenum catalyst having excellent catalytic activity or a typical quaternary bismuth-molybdenum catalyst with a relatively low number of metals and having excellent catalytic activity, the catalytic activity may be reduced due to the deformation of the structure.

Thus, the present invention provides the method of preparing a multicomponent bismuth-molybdenum composite metal oxide catalyst including the step of performing secondary co-precipitation which may provide good reproducibility of the preparation of the catalyst by facilitating the uniform formation of the metal components constituting the catalyst in the catalyst and may provide excellent catalytic activity even at a relatively lower temperature than a typical reaction temperature by appropriately controlling the oxidation ability while preventing the deformation of the structure of a typical quaternary bismuth-molybdenum catalyst.

A method of preparing a multicomponent bismuth-molybdenum composite metal oxide catalyst represented by the following Formula 1, according to an embodiment of the present invention, may include the steps of: preparing a first solution by mixing a divalent or trivalent cationic metal precursor solution, a monovalent cationic metal precursor solution, and a bismuth precursor solution (step 1); preparing a second solution by dropwise adding the first solution to a molybdenum precursor solution and performing primary co-precipitation (step 2); preparing a fourth solution by dropwise adding a third solution including a tetravalent cationic metal precursor during an aging process of the second solution and performing secondary co-precipitation (step 3); and sintering after drying the fourth solution (step 4).

$$[Mo_aBi_bC_cD_dE_eO_f]$$ [Formula 1]

where C represents a divalent or trivalent cationic metal element, D represents a monovalent cationic metal element, E represents a tetravalent cationic metal element, a is a real number of 5 to 20, b is a real number of 0.1 to 2, c is a real number of 1 to 5, d is a real number of 1 to 10, e is a real number of 0.1 to 1, and f is a value which is determined by other components to match valency.

Step 1 is a step of preparing a first solution by adding and mixing a precursor material of each metal component in a solvent in order to mix a divalent or trivalent cationic metal component, a monovalent cationic metal component, and a bismuth metal component which constitute a bismuth-molybdenum composite metal oxide catalyst. In this case, in order to uniformly mix the metal components, it may be desirable to prepare the first solution by respectively dissolving precursors of the metal components in a solvent to prepare each metal precursor solution and mixing the each metal precursor solution.

Specifically, a precursor of the divalent or trivalent cationic metal represented by C in Formula 1 is dissolved in a solvent to prepare a divalent or trivalent cationic metal precursor solution and, separately, a precursor of the monovalent cationic metal represented by D in Formula 1 is dissolved in a solvent to prepare a monovalent cationic metal precursor solution. In this case, the divalent or trivalent cationic metal precursor solution and the monovalent cationic metal precursor solution may be prepared by being separately dissolved in the solvents as described above, but a precursor solution, in a state in which the precursor of the divalent or trivalent cationic metal and the precursor of the monovalent cationic metal are simultaneously dissolved in one solvent and mixed, may be prepared. The solvent may be distilled water, but present invention is not limited thereto. Also, an acidic solution may be further added to increase solubility depending on the precursor of the each metal element, and the acidic solution is not particularly limited, but, for example, may be nitric acid.

The divalent or trivalent cationic metal represented by C in Formula 1 may be at least one metal selected from the group consisting of calcium (Ca), scandium (Sc), vanadium (V), chromium (Cr), manganese (Mn), iron (Fe), cobalt (Co), nickel (Ni), copper (Cu), zinc (Zn), gallium (Ga), germanium (Ge), and arsenic (As).

The monovalent cationic metal represented by D in Formula 1 may be at least one metal selected from the group consisting of lithium (Li), sodium (Na), potassium (K), rubidium (Rb), cesium (Cs), and francium (Fr).

For example, the divalent or trivalent cationic metal represented by C may be Fe, and the monovalent cationic metal represented by D may be K.

Any precursor may be used as the precursor of the divalent or trivalent cationic metal and the precursor of the monovalent cationic metal without particular limitation as long as it is typically used in the art, but the precursor of the divalent or trivalent cationic metal and the precursor of the monovalent cationic metal, for example, may include ammonium, carbonate, nitrate, acetate, and oxide of the each metal.

Like the divalent or trivalent cationic metal precursor solution and the monovalent cationic metal precursor solution, the bismuth precursor solution may be prepared by dissolving a precursor of bismuth metal in a solvent, and the solvent may be distilled water, a nitrate aqueous solution, or a mixture thereof, but the solvent is not particularly limited. In a case in which the solvent is distilled water, an acidic solution may be further added to increase solubility of the bismuth metal precursor and, in this case, the acidic solution is the same as described above.

Any precursor may be used as the precursor of bismuth metal without particular limitation as long as it is typically used in the art, but the precursor of bismuth metal, for example, may be bismuth nitrate.

The first solution, in which the each metal component is uniformly mixed, may be prepared by mixing the divalent or trivalent cationic metal precursor solution, the monovalent cationic metal precursor solution, and the bismuth precursor solution which are prepared by the above method. Any method may be used to perform the mixing without particular limitation as long as it is typically used in the art, but the mixing, for example, may be performed by stirring.

Step 2 is a step of preparing a second solution by dropwise adding the first solution to a molybdenum precursor solution and performing primary co-precipitation in order to co-precipitate the metal components by mixing the first solution and the molybdenum precursor solution.

Specifically, the molybdenum precursor solution may be prepared by dissolving a precursor of molybdenum metal in a solvent, and the solvent may be distilled water, but the present invention is not limited thereto.

Any precursor may be used as the precursor of molybdenum metal without particular limitation as long as it is typically used in the art, but the precursor of molybdenum metal, for example, may be ammonium molybdate.

The second solution may be prepared by dropwise adding the first solution to the molybdenum precursor solution prepared by the above method and performing primary co-precipitation.

The primary co-precipitation may be performed by slowly dropwise adding (injecting) the first solution at a constant rate to the molybdenum precursor solution while stirring.

Step 3 is a step of preparing a fourth solution by dropwise adding a third solution including a tetravalent cationic metal precursor while aging the second solution and performing secondary co-precipitation in order to co-precipitate a tetravalent cationic metal and simultaneously perform an aging process so that the co-precipitation of the metals included in the second solution is sufficiently performed.

The aging process is not particularly limited, but, for example, may be performed by stirring for 30 minutes to 24 hours while maintaining a temperature of 80° C. to 200° C. For example, the aging process may be performed by stirring for 1 hour to 2 hours.

The third solution including a tetravalent cationic metal precursor may be prepared by preparing a co-precipitation solution by dropwise adding a basic solution to a tetravalent cationic metal precursor solution and titrating to a pH of 5 to 9; and aging the co-precipitation solution by stirring for 30 minutes to 24 hours.

Specifically, the tetravalent cationic metal precursor solution may be prepared by dissolving a precursor of tetravalent cationic metal in a solvent, and the solvent may be distilled water.

The tetravalent cationic metal is represented by E in Formula 1 and may be represented by Formula 2 below.

$$[Ce_g Zr_{(1-g)}] \quad \text{[Formula 2]}$$

where g is a real number of 0.5 to 1.

That is, the tetravalent cationic metal may be cerium (Ce) or a mixture of Ce and zirconium (Zr), and, for example, may be the mixture of Ce and Zr.

In a case in which the tetravalent cationic metal is Ce, oxygen storability of the multicomponent bismuth-molybdenum composite metal oxide catalyst including Ce may be improved due to oxygen storage capacity of Ce, and, in a case in which the tetravalent cationic metal is the mixture of Ce and Zr, since Zr and Ce are mixed to increase oxygen mobility in the catalyst, the activity of the multicomponent bismuth-molybdenum composite metal oxide catalyst including the mixture of Ce and Zr may be increased.

Ce, as the tetravalent cationic metal element according to the present invention, is a material having oxygen storage capacity as described above, wherein, since Ce may increase the activity point of the catalyst by improving the oxygen storability of the multicomponent bismuth-molybdenum composite metal oxide catalyst including Ce, the catalytic activity may be improved. Also, in the case that the tetravalent cationic metal is the mixture of Ce and Zr, Zr may further improve the activity of the catalyst by increasing the oxygen mobility in the catalyst, that is, by adjusting the number of lattice oxygens consumed during the reaction. Thus, excellent catalytic activity may be obtained even at a relatively low reaction temperature.

Furthermore, in the case that the tetravalent cationic metal is the mixture of Ce and Zr, a molar ratio of the Ce to the Zr may be in a range of 0.5:0.5 to 0.75:0.25, and, for example, the Ce and Zr may have a molar ratio of Ce:Zr of 0.65:0.35.

When the Ce and Zr have the above molar ratio, since the number of the lattice oxygens consumed in the reaction may be adjusted by appropriately controlling the oxygen mobility and oxygen storability of the multicomponent bismuth-molybdenum composite metal oxide catalyst including Ce and Zr, high hydrothermal stability may be obtained, and the formation of by-products may be reduced and the conversion rate of reactant and the yield of desired product may be further improved in the catalytic reaction process using the above catalyst.

Any precursor may be used as the precursor of tetravalent cationic metal without particular limitation as long as it is typically used in the art, and the precursor of tetravalent cationic metal, for example, may be ammonium, carbonate, nitrate, acetate, and oxide of the metal.

As described above, the third solution may be prepared by dropwise adding a basic solution to a tetravalent cationic metal precursor solution and adjusting the pH to prepare a co-precipitation solution and then aging the co-precipitation solution, wherein any basic solution may be used as the basic solution without particular limitation as long as it is typically used in the art, and the basic solution, for example, may be a sodium hydroxide aqueous solution, ammonia water, a sodium carbonate aqueous solution, or a potassium carbonate aqueous solution.

The pH may be in a range of 5 to 9, for example, 7 to 8.

The aging is not particularly limited, but may be performed by stirring for 30 minutes to 24 hours, for example, 1 hour to 2 hours.

The fourth solution according to the present invention may be prepared by dropwise adding the third solution prepared by the above method to the second solution during the aging process and performing the secondary co-precipitation. In this case, the third solution may be slowly injected dropwise into the second solution at a constant rate.

That is, the third solution may be co-precipitated during the aging process of the second solution and may be mixed and aged with the second solution.

Step 4 is a step of drying and sintering the fourth solution in order to obtain a multicomponent bismuth-molybdenum composite metal oxide catalyst from the prepared fourth solution.

The drying may be performed by performing a heat treatment at a temperature of 150° C. to 200° C. for 10 hours to 24 hours after removing a liquid component from the fourth solution, and the present invention is not limited thereto.

Any method may be used as a method of removing the liquid component without particular limitation as long as it is typically used in the art, but, for example, the liquid component may be removed using vacuum or a centrifugal concentrator.

The sintering may be performed by performing a heat treatment at a temperature of 400° C. to 600° C. in an air atmosphere.

In the preparation method according to the present invention, since the metal components are not co-precipitated at a time but are co-precipitated in two steps, i.e., primary and secondary co-precipitation, the primary co-precipitated metal catalyst components (quaternary bismuth-molybdenum catalyst metal components) and the metal catalyst component (Ce—Zr or Ce) mixed by the secondary co-precipitation may be uniformly mixed to increase the reproducibility of the preparation of the catalyst. Also, since the almost same structure as a typical quaternary bismuth-molybdenum catalyst may be maintained, the stability of the catalyst may be excellent and the reduction of the catalytic activity due to the deformation of the structure of the catalyst may be suppressed.

Furthermore, the present invention provides a multicomponent bismuth-molybdenum composite metal oxide catalyst represented by the following Formula 1 which is prepared by the above method.

$$[Mo_aBi_bC_cD_dE_eO_f]$$  [Formula 1]

where C, D, E, a, b, c, d, e, and f are the same as described above.

In Formula 1, a may be between 5 and 20, b may be between 0.1 and 2, c may be between 1 and 5, d may be between 1 and 10, and e may be between 0.1 and 1. For example, a may be between 9 and 15, b may be between 0.5 and 1.5, c may be between 2 and 4, d may be between 1 and 5, and e may be between 0.1 and 2. That is, each metal component constituting the multicomponent bismuth-molybdenum composite metal oxide catalyst may have a ratio of Mo:Bi:C:D:E of 5:0.1:1:1:0.1 to 20:2:5:10:1, preferably, 9:0.5:2:1:0.1 to 15:1.5:4:5:1. For example, the ratio of Mo:Bi:C:D:E may be 10:1:3:1:1.

When the metal components constituting the multicomponent bismuth-molybdenum composite metal oxide catalyst have the above ratio, since the mechanical properties and hydrothermal stability of the catalyst are improved and the oxygen storability and oxygen mobility in the catalyst are appropriately controlled, the formation of by-products may be reduced and the conversion rate of reactant and the yield of desired product may be further improved in the catalytic reaction process using the above catalyst.

The catalyst may be an oxidative dehydrogenation catalyst and, for example, may be an oxidative dehydrogenation catalyst for preparing 1,3-butadiene.

In addition, the present invention provides a method of preparing 1,3-butadiene using the above-described multicomponent bismuth-molybdenum composite metal oxide catalyst.

A method of preparing 1,3-butadiene according to an embodiment of the present invention may include the following steps of:

filling a reactor with a multicomponent bismuth-molybdenum composite metal oxide catalyst as a stationary phase (step A); and performing oxidative dehydrogenation while continuously passing a reactant, which contains a C4 compound including n-butene, through a catalyst layer of the reactor filled with the catalyst (step B).

The oxidative dehydrogenation may be performed at a reaction temperature of 250° C. to 380° C. and a space velocity of 50 h$^{-1}$ to 2,000 h$^{-1}$ based on the n-butene.

Hereinafter, the present invention will be described in more detail according to the following examples and experimental examples. However, the following examples and experimental examples are merely presented to exemplify the present invention, and the scope of the present invention is not limited thereto.

EXAMPLE

A hexanary bismuth-molybdenum composite metal oxide catalyst was prepared by a preparation method through a two-step co-precipitation process including primary co-precipitation and secondary co-precipitation steps.

First, ferric nitrate nonahydrate (Fe(NO$_3$)$_3$.9H$_2$O) and potassium nitrate (KNO$_3$) were dissolved in distilled water to prepare an iron and potassium precursor mixed solution. Separately, bismuth nitrate pentahydrate (Bi(NO$_3$)$_3$.5H$_2$O) was dissolved in a nitrate aqueous solution to prepare a bismuth precursor solution, and the iron and potassium precursor mixed solution was dropwise added thereto to prepare a first solution. Thereafter, the first solution was slowly dropwise added to a molybdenum precursor solution which was prepared by dissolving ammonium molybdenum tetrahydrate ((NH$_4$)$_6$(Mo$_7$O$_{24}$).4H$_2$O) in distilled water, and primary co-precipitation was performed to prepare a second solution. In order to allow the co-precipitation of the metal components in the second solution to be sufficiently performed, the second solution was aged by stirring for 2 hours while maintaining the second solution at 100° C. In this case, cerium nitrate hexahydrate (Ce(NO$_3$)$_3$.6H$_2$O) and zirconium nitrate hexahydrate (ZrO(NO$_3$)$_2$.6H$_2$O) were dissolved in distilled water in a separate reaction vessel, and the solution thus obtained was titrated to a pH of 7 by adding a 0.1 N sodium hydroxide aqueous solution and then stirred for 1 hour to prepare a third solution including cesium precursor and zirconium precursor. The third solution was slowly dropwise added to the second solution during the aging and secondary co-precipitation was performed to prepare a fourth solution. In this case, the third solution was prepared by adding a precursor material of each metal so that a molar ratio of Ce to Zr was 0.65:0.35. Water and other liquid components were removed from the fourth solution after the completion of the aging by vacuum evaporation to obtain a solid, and the solid was dried at 180° C. for 8 hours and then sintered at 450° C. for 8 hours in an air atmosphere to prepare a hexanary bismuth-molybdenum composite metal oxide catalyst [Mo$_{10}$Bi$_1$Fe$_3$K$_1$Ce$_{0.1}$Zr$_{0.05}$O$_{37}$].

Comparative Example 1

Ferric nitrate nonahydrate (Fe(NO$_3$)$_3$.9H$_2$O) and potassium nitrate (KNO$_3$) were dissolved in distilled water to prepare an iron and potassium precursor mixed solution. Separately, bismuth nitrate pentahydrate (Bi(NO$_3$)$_3$.5H$_2$O) was dissolved in a nitrate aqueous solution to prepare a bismuth precursor solution, and the iron and potassium precursor mixed solution was dropwise added thereto to prepare a first solution. Thereafter, the first solution was slowly dropwise added to a molybdenum precursor solution which was prepared by dissolving ammonium molybdenum tetrahydrate ((NH$_4$)$_6$(Mo$_7$O$_{24}$).4H$_2$O) in distilled water, and co-precipitation was performed to prepare a second solution. In order to allow the co-precipitation of the metal components in the second solution to be sufficiently performed, the second solution was aged by stirring for 2 hours while maintaining the second solution at 100° C. Water and other liquid components were removed from the second solution after the completion of the aging by vacuum evaporation to obtain a solid, and the solid was dried at 180° C. for 8 hours and then sintered at 450° C. for 8 hours in an air atmosphere to prepare a quaternary bismuth-molybdenum composite metal oxide catalyst [Mo$_{10}$Bi$_1$Fe$_3$K$_1$O$_{37}$].

Comparative Example 2

Ferric nitrate nonahydrate (Fe(NO$_3$)$_3$.9H$_2$O), potassium nitrate (KNO$_3$), cerium nitrate hexahydrate (Ce(NO$_3$)$_3$.6H$_2$O), and zirconium nitrate hexahydrate (ZrO(NO$_3$)$_2$. 6H$_2$O) were dissolved in distilled water to prepare an iron, potassium, cerium, and zirconium precursor mixed solution. In this case, the cerium nitrate hexahydrate and the zirconium nitrate hexahydrate were added so that a molar ratio of cerium to zirconium in the finally prepared catalyst was 0.65:0.35. Separately, bismuth nitrate pentahydrate (Bi(NO$_3$)$_3$.5H$_2$O) was dissolved in a nitrate aqueous solution to prepare a bismuth precursor solution, and the iron and potassium precursor mixed solution was dropwise added thereto to prepare a first solution. Thereafter, the first solution was slowly dropwise added to a molybdenum precursor solution which was prepared by dissolving ammonium molybdenum tetrahydrate $((NH_4)_6(Mo_7O_{24})\cdot 4H_2O)$ in distilled water, and co-precipitation was performed to prepare a second solution. In order to allow the co-precipitation of the metal components in the second solution to be sufficiently performed, the second solution was aged by stirring for 2 hours while maintaining the second solution at 100° C. Water and other liquid components were removed from the second solution after the completion of the aging by vacuum evaporation to obtain a solid, and the solid was dried at 180° C. for 8 hours and then sintered at 450° C. for 8 hours in an air atmosphere to prepare a hexanary bismuth-molybdenum composite metal oxide catalyst $[Mo_{10}Bi_1Fe_3K_1Ce_{0.1}Zr_{0.05}O_{37}]$.

Experimental Example 1

Figure 2:
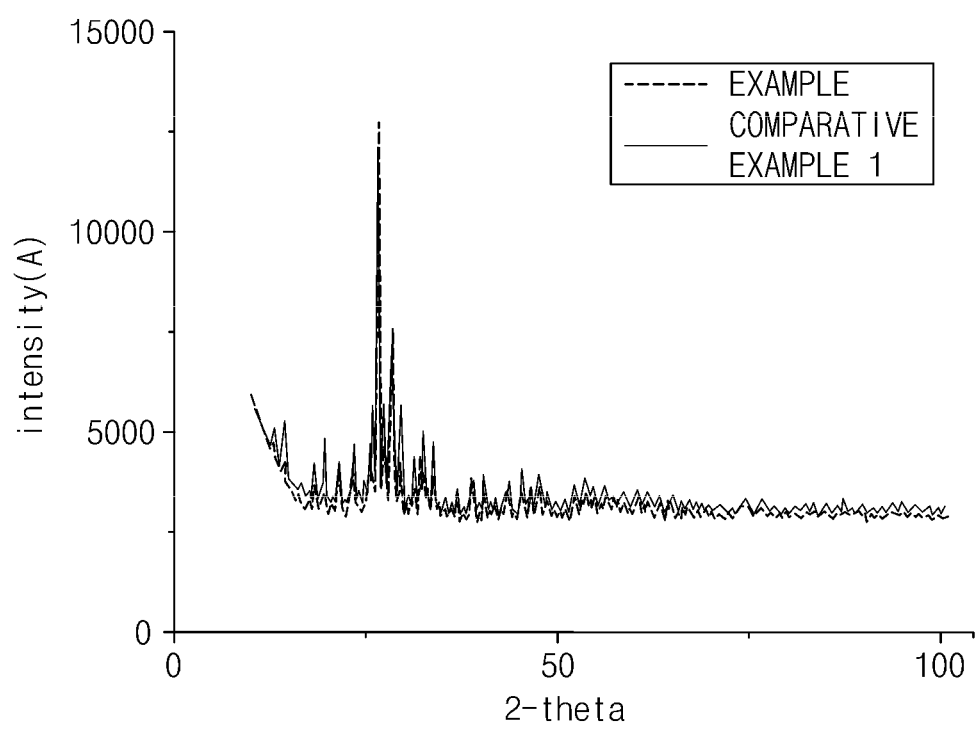
FIG. 2 is a graph illustrating results of X-ray (XRD) analysis of the multicomponent bismuth-molybdenum composite metal oxide catalyst according to the embodiment of the present invention.
Figure 3:
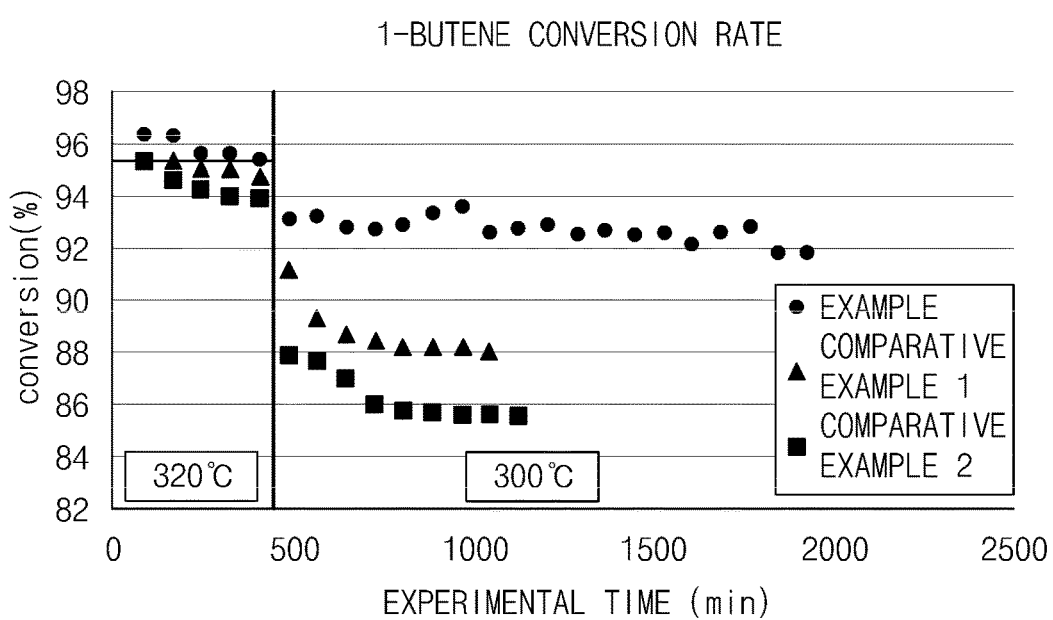
FIG. 3 is a graph illustrating a conversion rate of 1-butene among results of each catalytic reaction process using a hexanary bismuth-molybdenum composite metal oxide catalyst (Example) prepared through two-step co-precipitation according to an embodiment of the present invention, a quaternary bismuth-molybdenum composite metal oxide catalyst (Comparative Example 1), and a hexanary bismuth-molybdenum composite metal oxide catalyst (Comparative Example 2) prepared through one-step co-precipitation.
Figure 4:
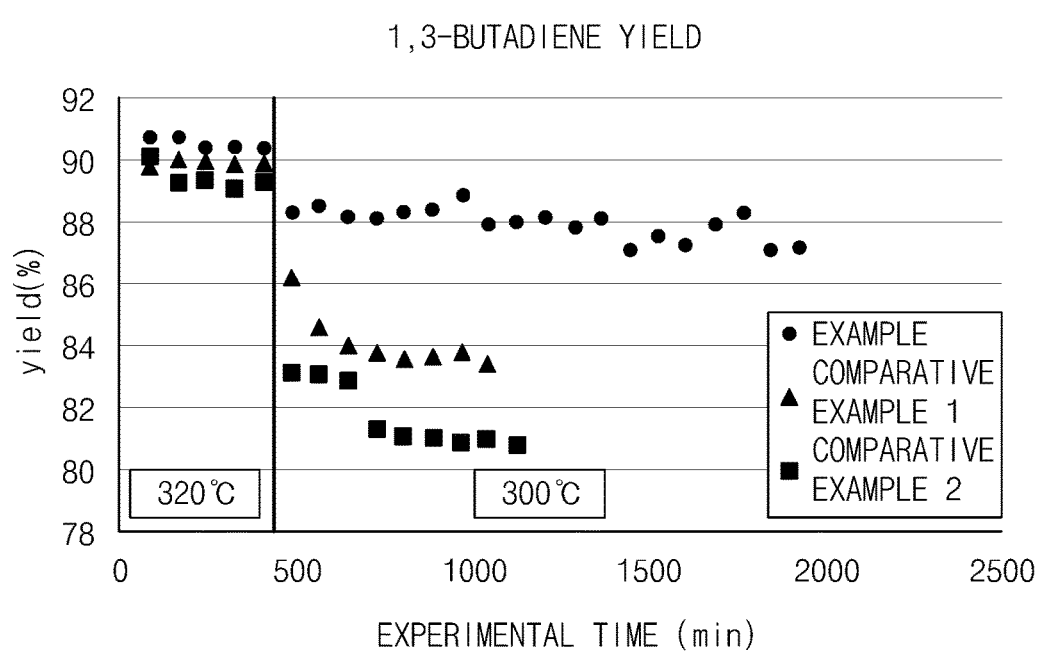
FIG. 4 is a graph illustrating a yield of 1,3-butadiene among the results of each catalytic reaction process using the hexanary bismuth-molybdenum composite metal oxide catalyst (Example) prepared through the two-step co-precipitation according to the embodiment of the present invention, the quaternary bismuth-molybdenum composite metal oxide catalyst (Comparative Example 1), and the hexanary bismuth-molybdenum composite metal oxide catalyst (Comparative Example 2) prepared through the one-step co-precipitation.
Figure 5:
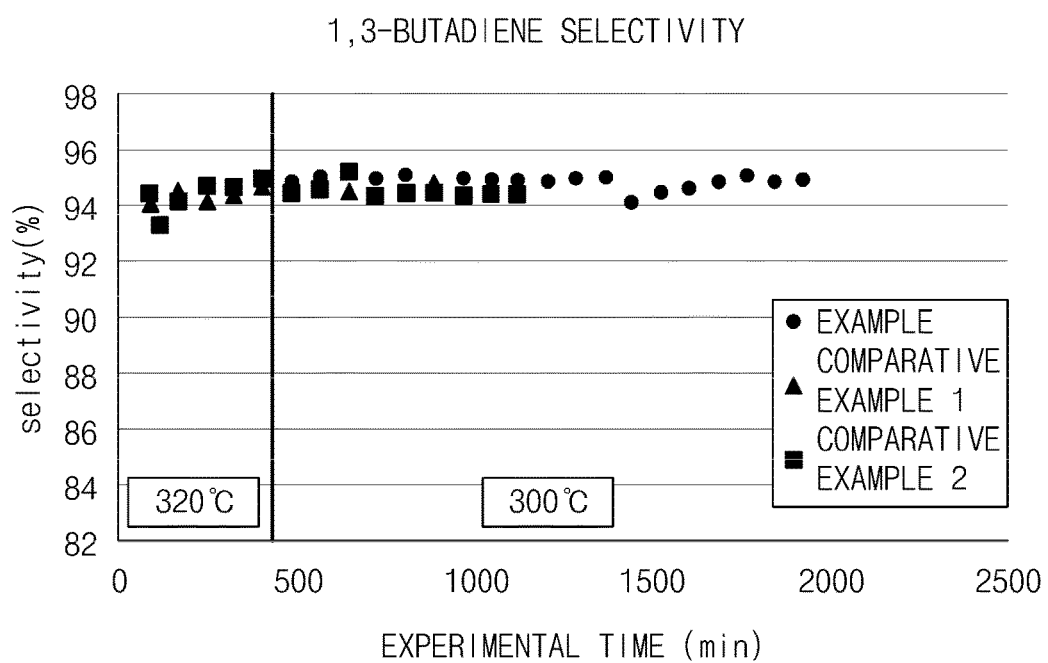
FIG. 5 is a graph illustrating 1,3-butadiene selectivity among the results of each catalytic reaction process using the hexanary bismuth-molybdenum composite metal oxide catalyst (Example) prepared through the two-step co-precipitation according to the embodiment of the present invention, the quaternary bismuth-molybdenum composite metal oxide catalyst (Comparative Example 1), and the hexanary bismuth-molybdenum composite metal oxide catalyst (Comparative Example 2) prepared through the one-step co-precipitation.
Figure 6:
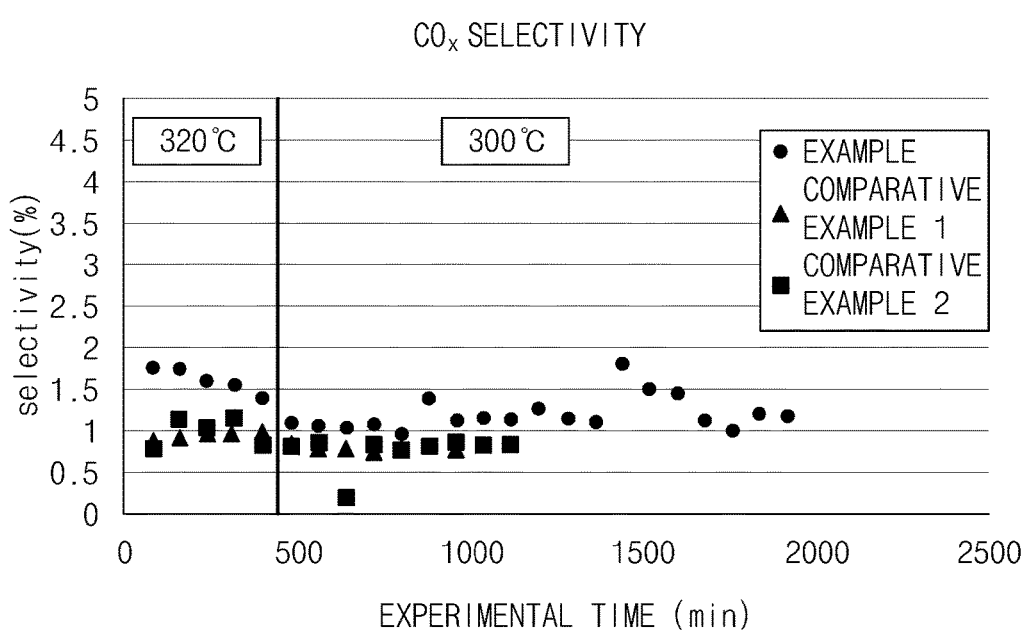
FIG. 6 is a graph illustrating $CO_x$ selectivity among the results of each catalytic reaction process using the hexanary bismuth-molybdenum composite metal oxide catalyst (Example) prepared through the two-step co-precipitation according to the embodiment of the present invention, the quaternary bismuth-molybdenum composite metal oxide catalyst (Comparative Example 1), and the hexanary bismuth-molybdenum composite metal oxide catalyst (Comparative Example 2) prepared through the one-step co-precipitation.
Figure 7:
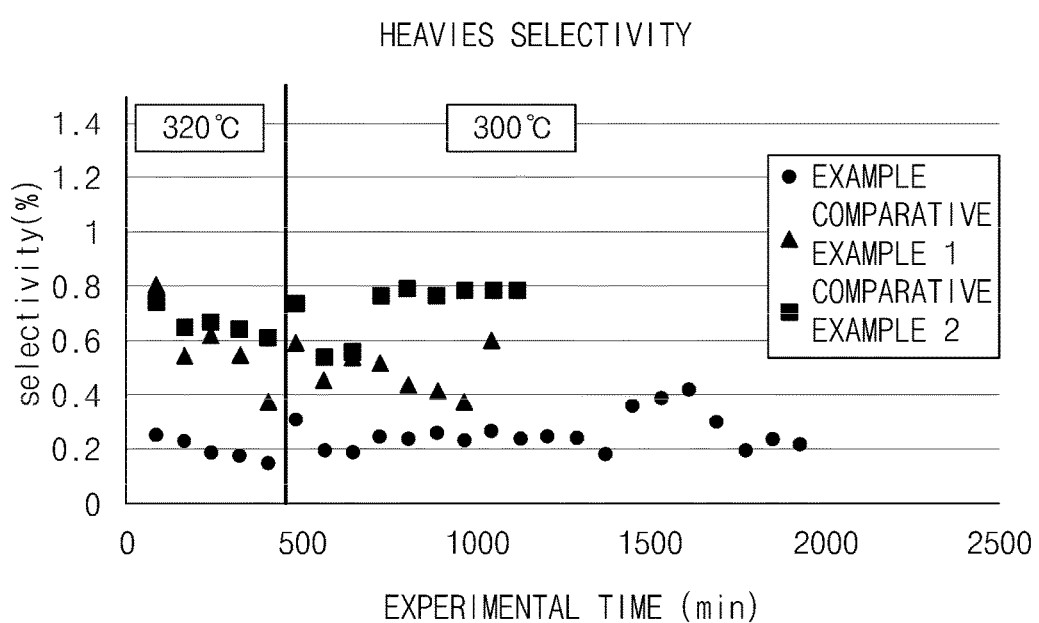
FIG. 7 is a graph illustrating heavies selectivity among the results of each catalytic reaction process using the hexanary bismuth-molybdenum composite metal oxide catalyst (Example) prepared through the two-step co-precipitation according to the embodiment of the present invention, the quaternary bismuth-molybdenum composite metal oxide catalyst (Comparative Example 1), and the hexanary bismuth-molybdenum composite metal oxide catalyst (Comparative Example 2) prepared through the one-step co-precipitation.

X-ray diffraction (XRD) analysis was performed to compare and analyze structural characteristics of the hexanary bismuth-molybdenum composite metal oxide catalyst prepared in Example and the quaternary bismuth-molybdenum composite metal oxide catalyst prepared in Comparative Example 1, and the results thereof are presented in FIG. 2. The XRD analysis was performed by using a Bruker AXS D4 Endeavor XRD (voltage of 40 KV, current of 40 mA, Cu-target tube, wavelength of 1.5418 Å, and LynxEye position sensitive detector (3.7° slit)), a fixed divergence slit (FDS) of 0.5° was used, and intensities were measured in steps of 0.02° for 87.5 seconds in the 2 theta range of 10° to 100°.

As illustrated in FIG. 2, the hexanary bismuth-molybdenum composite metal oxide catalyst of Example prepared by the method using two-step co-precipitation according to the present invention had the almost same structure as the quaternary bismuth-molybdenum composite metal oxide catalyst (Comparative Example 1) which did not include a tetravalent cationic metal. This indicated that since the metal components constituting the catalyst were co-precipitated in two steps instead of being co-precipitated at a time, the deformation of the structure of the catalyst may not occur. Thus, this indicated that the reduction of the catalytic activity due to the deformation of the structure may be prevented.

Experimental Example 2

In order to compare and analyze activity of each catalyst prepared in Example and Comparative Examples 1 and 2, a conversion rate of 1-butene, a yield of 1,3-butadiene, 1,3-butadiene selectivity, heavies selectivity, and $CO_X$ selectivity were measured by the following methods.

1-butene and oxygen were used as reactants and, in addition, nitrogen and steam were introduced therewith. A metal tubular reactor was used as a reactor.

Ratio and gas hourly space velocity (GHSV) of the reactants were described on the basis of 1-butene. A ratio of 1-butene:oxygen:steam:nitrogen was set as 1:1:4:12 and the gas hourly space velocity was constantly adjusted to 100 $h^{-1}$. A volume of a catalyst layer in contact with the reactants was fixed to 200 cc, and a reaction apparatus was designed so that water was injected into a vaporizer and vaporized into steam at 340° C. to be mixed with other reactants, 1-butene and oxygen, and introduced into the reactor. An amount of 1-butene was controlled by using a mass flow controller for liquids, oxygen and nitrogen were controlled by using a mass flow controller for gases, and an amount of steam was controlled by adjusting an injection rate using a liquid pump. A reaction was performed by changing a reaction temperature, wherein the reaction was performed for 6 hours while maintaining the temperature at 320° C. at a pressure of 12 psig and the reaction was then continuously performed after the temperature was decreased to 300° C. A product after the reaction was analyzed by gas chromatography. The conversion rate of 1-butene and the yield of 1,3 butadiene were calculated by the following Equations 1 and 2, respectively. The results thereof are presented in Table 1 and FIGS. 3 to 7 below.

$$\text{Conversion rate (\%)} = \frac{\text{number of moles of 1-butene reacted}}{\text{number of moles of 1-butene supplied}} \times 100 \quad [\text{Equation 1}]$$

$$\text{Yield (\%)} = \frac{\text{number of moles of 1, 3-butadiene formed}}{\text{number of moles of 1-butene supplied}} \times 100 \quad [\text{Equation 2}]$$

TABLE 1

|  | Example | Comparative Example 1 | Comparative Example 2 |
| --- | --- | --- | --- |
| Category (reaction temperature: 320° C.) |  |  |  |
| 1-butene conversion rate (%) | 95.85 | 95.17 | 94.42 |
| 1,3-butadiene yield (%) | 90.59 | 89.96 | 89.42 |
| 1,3-butadiene selectivity | 94.52 | 94.52 | 94.70 |
| Heavies selectivity | 0.21 | 0.59 | 0.67 |
| $CO_x$ selectivity | 1.63 | 0.96 | 1.01 |
| Category (reaction temperature: 300° C.) |  |  |  |
| 1-butene conversion rate (%) | 92.71 | 88.88 | 86.35 |
| 1,3-butadiene yield (%) | 88.04 | 84.18 | 81.72 |
| 1,3-butadiene selectivity | 94.96 | 94.72 | 94.64 |
| Heavies selectivity | 0.27 | 0.50 | 0.73 |
| $CO_x$ selectivity | 1.22 | 0.82 | 0.76 |

As illustrated in Table 1 and FIGS. 3 to 7, it was confirmed that the hexanary bismuth-molybdenum composite metal oxide catalyst of Example prepared by the method using two-step co-precipitation according to the present invention exhibited excellent catalytic activity in the overall reaction temperature range in comparison to the quaternary bismuth-molybdenum composite metal oxide catalyst of Comparative Example 1 which did not include Ce—Zr and the hexanary bismuth-molybdenum composite metal oxide catalyst of Comparative Example 2 which was composed of the same components but was prepared by the method using one-step co-precipitation.

Specifically, the hexanary bismuth-molybdenum composite metal oxide catalyst of Example according to the present invention exhibited significantly lower heavies selectivity and slightly better catalytic activity (1-butene conversion rate, 1,3-butadiene yield, and 1,3-butadiene selectivity) than the quaternary bismuth-molybdenum composite metal oxide catalyst of Comparative Example 1 and the hexanary bismuth-molybdenum composite metal oxide catalyst of Comparative Example 2 in a reaction process at the reaction temperature of 320° C. while maintaining low CO$_x$ selectivity similar to those of the catalysts of Comparative Example 1 and Comparative Example 2.

Also, at a relatively low temperature of 300° C., the hexanary bismuth-molybdenum composite metal oxide catalyst of Example according to the present invention had a significantly improved conversion rate of 1-butene as well as a yield of 1,3-butadiene while exhibiting lower heavies selectivity than the quaternary bismuth-molybdenum composite metal oxide catalyst of Comparative Example 1 and the hexanary bismuth-molybdenum composite metal oxide catalyst of Comparative Example 2.

The reason for this is that, with respect to the hexanary bismuth-molybdenum composite metal oxide catalyst according to the present invention, since Ce—Zr, a component having oxygen storability and oxygen mobility, was added, there was an effect of improving the catalytic activity in comparison to the typical quaternary bismuth-molybdenum composite metal oxide catalyst (Comparative Example 1). Also, since the catalyst was prepared by performing the co-precipitation of the metal components constituting the catalyst in two steps instead of performing the co-precipitation at a time, the reduction of the catalytic activity due to the deformation of the structure of the catalyst may be suppressed and the number of lattice oxygens may be simultaneously adjusted by including the component having oxygen storability and oxygen mobility without the deformation of the structure of the catalyst. Thus, there was an effect of improving the catalytic activity in comparison to the hexanary bismuth-molybdenum composite metal oxide catalyst (Comparative Example 2) which had the same components, but was prepared by one-step co-precipitation.

The invention claimed is:

1. A method of preparing a multicomponent bismuth-molybdenum composite metal oxide catalyst, the method comprising:
    (1) preparing a first solution by:
        a) dissolving a precursor of a divalent or a trivalent cationic metal in a solvent to prepare a divalent or trivalent cationic metal precursor solution, where the divalent or trivalent cationic metal is at least one metal selected from the group consisting of scandium (Sc), vanadium (V), iron (Fe), copper (Cu), gallium (Ga), germanium (Ge), and arsenic (As);
        b) separately dissolving a precursor of a monovalent cationic metal in a solvent to prepare a monovalent cationic metal precursor solution, where the monovalent cationic metal is at least one metal selected from the group consisting of lithium (Li), sodium (Na), potassium (K), rubidium (Rb), and cesium (Cs);
        c) dissolving a bismuth precursor in a solvent to prepare a bismuth precursor solution; and
        d) mixing the divalent or trivalent cationic metal precursor solution, the monovalent cationic metal precursor solution, and the bismuth precursor solution to yield the first solution;
    (2) preparing a second solution by:
        a) preparing an aqueous molybdenum precursor solution containing only a molybdenum precursor by dissolving the molybdenum precursor solution in water; and
        b) dropwise adding the first solution to the molybdenum precursor solution and performing primary co-precipitation to yield the second solution;
    (3) preparing a fourth solution by dropwise adding a third solution comprising a tetravalent cationic metal precursor to the second solution during an aging process of the second solution and performing a secondary co-precipitation; and
    (4) sintering after drying the fourth solution to yield a multicomponent bismuth-molybdenum composite metal oxide catalyst of Formula 1:

[Mo$_a$Bi$_b$C$_c$D$_d$E$_e$O$_f$]     [Formula 1]

wherein:
        C represents the divalent or trivalent cationic metal,
        D represents the monovalent cationic metal,
        E represents the tetravalent cationic metal,
        a is a real number of 5 to 20, b is a real number of 0.1 to 2, c is a real number of 1 to 5, d is a real number of 1 to 10, e is a real number of 0.1 to 1, and f is a value which is determined by other components to match valency.

2. The method of claim 1, wherein the third solution is prepared by:
    preparing a co-precipitation solution by dropwise adding a basic solution to a tetravalent cationic metal precursor solution and titrating to a pH of 5 to 9; and
    aging the co-precipitation solution by stirring for 30 minutes to 24 hours.

3. The method of claim 1, wherein the aging process of step (3) is performed by stirring for 30 minutes to 24 hours while maintaining a temperature of 80° C. to 200° C.

4. The method of claim 1, wherein the drying of step (4) is performed by performing a heat treatment at a temperature of 150° C. to 200° C. after removing a liquid component from the fourth solution.

5. The method of claim 1, wherein the sintering of step (4) is performed by performing a heat treatment at a temperature of 400° C. to 600° C. in an air atmosphere.

6. The method of claim 1, wherein C is Fe and D is K.

7. The method of claim 1, wherein the tetravalent cationic metal element represented by E is represented by Formula 2:

[Ce$_g$Zr$_{(1-g)}$]     [Formula 2]

wherein g is a real number of 0.5 to 1.

8. The method of claim 1, wherein E is cerium (Ce) and zirconium (Zr), and
    a molar ratio of the Ce to the Zr is in a range of 0.5:0.5 to 0.75:0.25.

9. The method of claim 1, wherein a is 9 to 15, b is 0.5 to 1.5, c is 2 to 4, d is 1 to 5, and e is 0.1 to 1.

* * * * *